United States Patent [19]

Portnoy

[11] 4,431,419
[45] Feb. 14, 1984

[54] DENTURE MAGNETIC RETENTION UNIT

[76] Inventor: Leonard L. Portnoy, 8820 Wilshire Blvd., Ste. 303, Beverly Hills, Calif. 90211

[21] Appl. No.: 471,057

[22] Filed: Mar. 1, 1983

[51] Int. Cl.$^3$ ............................................. A61C 13/22
[52] U.S. Cl. ..................................................... 433/189
[58] Field of Search ........................................ 433/189

[56] References Cited

U.S. PATENT DOCUMENTS 3,646,676 3/1972 Mitchell ............................... 433/189
4,302,189 11/1981 Gillings ................................. 433/189

*Primary Examiner*—Robert Peshock
*Attorney, Agent, or Firm*—Keith D. Beecher

[57] ABSTRACT

A closed field magnetic denture retention unit which includes a ferromagnetic cup containing a cylindrical permanent magnet which is displaced down from the top of the cup, the cup and magnet being embedded in the denture; and a magnetic keeper which is embedded in an exposed tooth root in the mouth of a patient and extends across the top of the cup in contact with the peripheral edge of the cup but not with the magnet, the keeper serving to close the cup when the denture is in place to retain the denture in place by magnetic attraction, the keeper forming a closed magnetic field so that there is no external magnetic field in the mouth of the patient.

7 Claims, 2 Drawing Figures

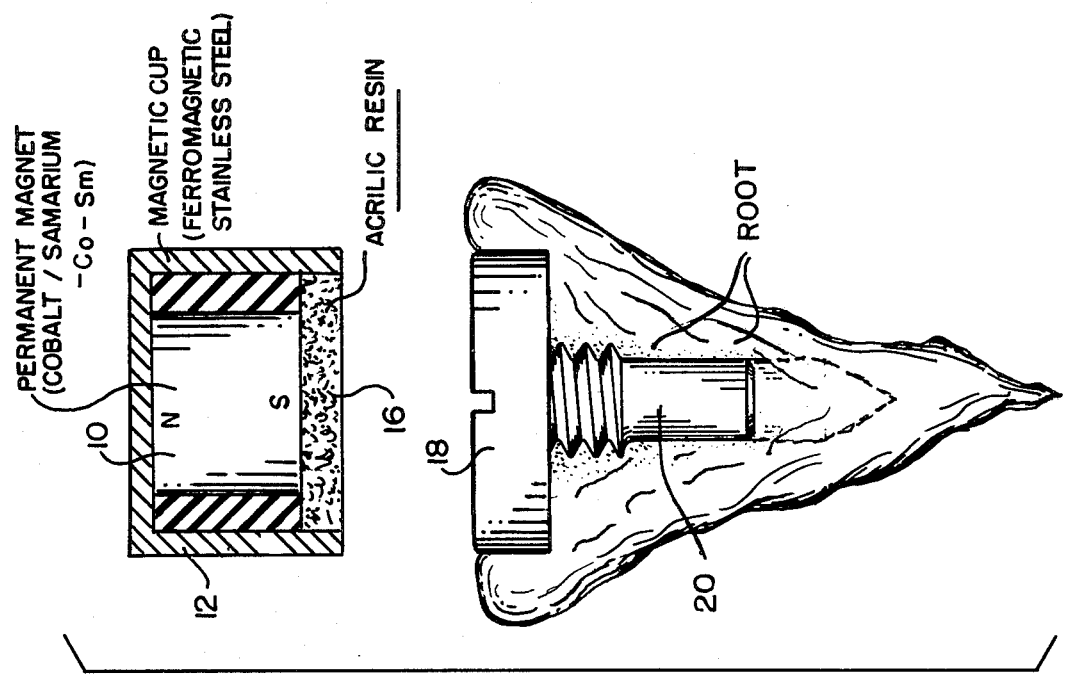
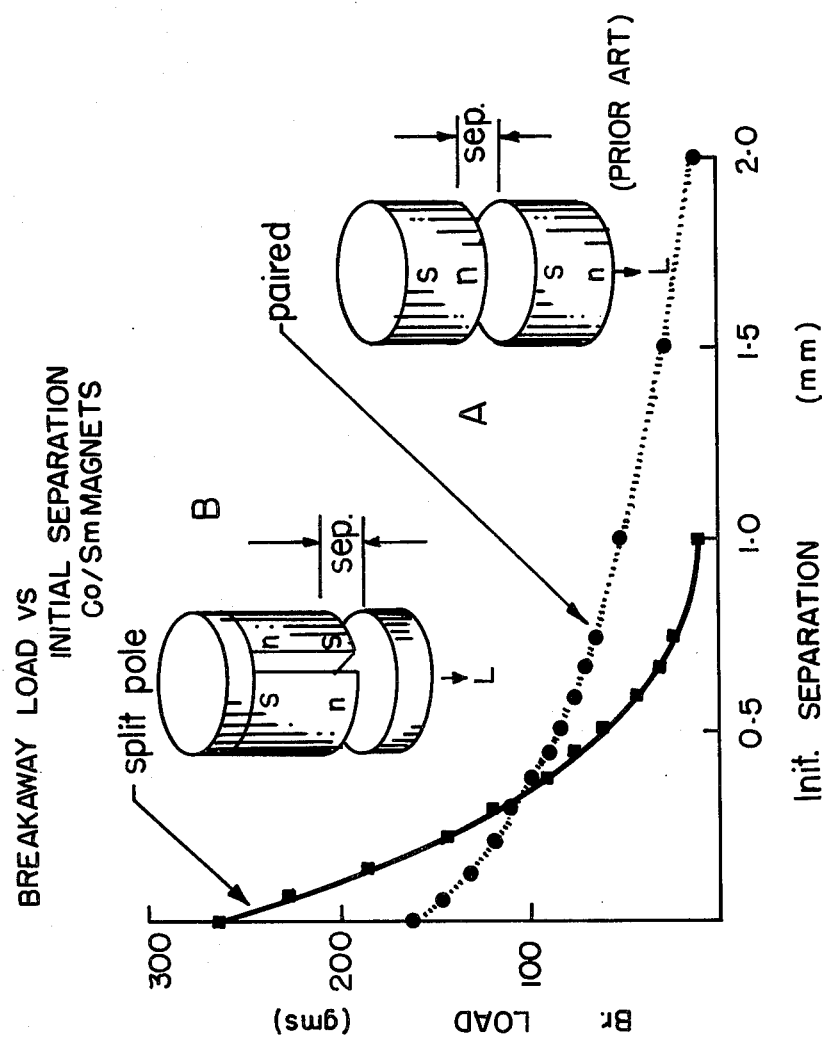

DENTURE MAGNETIC RETENTION UNIT

BACKGROUND OF THE INVENTION

Certain types of prior art magnetic denture retention devices have been developed by Dr. Barrie R. D. Gillings of the University of Malaya in Malaysia, these being described in his U.S. Pat. Nos. 4,209,905 and 4,302,189. As described in various publications by Dr. Gillings, the use of permanent magnets as denture retention devices is known to the art. For example, paired bar permanent magnets, embedded into the maxillary and mandibular dentures, have been used in the art for denture retention, through the mutual repulsion of like poles of the magnets. Permanent magnets have also been used as implants in the bone of the lower jaw as retention aids for mandibular dentures containing opposite polarity magnets, so that magnetic attraction will occur between the implanted magnets and the magnets in the dentures.

Recently, a new magnetic alloy, composed of cobalt and samarium ($CO_5Sm$) has become available. Permanent magnets made from this alloy not only exhibit extremely high magnetic field strength, but they also possess extremely high coercivity. This coercivity is so high in cobalt/samarium magnets that the magnets can be made extremely short without the north pole tending to demagnetize the south pole. This unique property is such that cylindrical-shaped permanent magnets of a diameter, for example, of 3 millimeters, and of a length of 2 to 3 millimeters, can provide magnetic attraction forces in excess of 300 grams. This property of the cobalt/samarium magnet renders it ideal for use in the unit of the present invention.

It is widely believed that the magnetic fields produced by permanent magnets can damage tissues, when such magnets are used in patients' mouths. This belief has inhibited the use of permanent magnets for denture retention purposes in the past. However, Dr. Gillings in the publications referred to above describes magnetic type denture retention units which do not exhibit any significant external magnetic field, so as to remove any objection to the use of his devices for denture retention purposes.

The Gillings closed field magnetic retention unit comprises a pair of oppositely-poled permanent magnets, preferably of the cobalt/samarium type placed adjacent to one another in a slightly spaced relationship. A first ferromagnetic keeper is placed across one end of the two magnets in contact with the magnets to form a first magnetic path between the opposite poles of the two magnets at that end. In accordance with Dr. Gillings' teachings, the two magnets and the first keeper are embedded in the denture with the two pole faces at the opposite ends of the magnets being exposed at the surface of the denture. A second keeper of ferromagnetic material is embedded in the patient's mouth in the root of a tooth which serves as an anchor for the denture. When the denture is in place, it is magnetically retained on the root because of the magnetic attraction of the second keeper and the permanent magnets. Moreover, the resulting assembly produces a closed magnetic circuit from the poles of the permanent magnets through the two keepers, so that there is no external magnetic field.

The unit of the present invention achieves the same results as the Gillings' unit, but by means of a unit which may be more simply constructed than the Gillings' unit, and which has inherent features which are not present in the Gillings' unit.

BRIEF DESCRIPTION OF THE DRAWINGS

FIG. 1 is a representation of various graphs, exhibiting the action of the prior art open field type of magnetic retention unit, and of the prior art Gillings type of closed field magnetic retention unit; and FIG. 2 is a representation, partly in section, of the magnetic denture retention unit of the present invention in one of its embodiments.

DETAILED DESCRIPTION OF THE ILLUSTRATED EMBODIMENT

Although many researchers believe that magnetic fields have no adverse affect on human tissues and that magnetism is completely innocuous to tissues, there is a considerable body of literature suggesting that magnetic fields can exert adverse tissue effects.

In the prior art magnet-to-magnet retention unit such as designated A in FIG. 1, an external magnetic field is generated which may be as high as 30 milliteslas at the gingival margin, which some investigators believe to be too high for permanent clinical applications.

The Gillings retention unit, as shown as B in FIG. 1, comprises a pair of split cylindrical-shaped permanent magnets placed in side-to-side space relationship, and oppositely poled; the magnets being provided with magnetizable, low coercivity, end plates or keepers. The keepers may be formed of ferromagnetic stainless steel of, for example, the 400 Series. These stainless steel keepers provide a closed field pathway for the magnetic fields produced by the magnets, and they substantially eliminate any external magnetic field.

In the prior art unit A of FIG. 1, one of the permanent magnets is embedded in the denture to be retained, and the other is fastened to the anchoring root. In the Gillings unit shown as B in FIG. 1, the two magnets and the upper keeper are embedded in the denture, and the lower keeper is embedded in the root. The breakaway load versus initial separation, of both units A and B, using cobalt/samarium magnets, is shown in the accompanying graphs in FIG. 1.

In the magnetic unit of the present invention, as shown in FIG. 2, a closed magnetic field is obtained by use of a simple disc-shaped permanent magnet, with no need to split the magnet as is the case with the Gillings device.

In the unit of the present invention, a disc-shaped permanent magnet 10 is retained in a cup-shaped member 12. The magnet 10 may be formed, for example, of a cobalt/samarium alloy. The cup 12 may be formed of any appropriate magnetic material of low coercivity, such as ferromagnetic stainless steel, for example, of the 400 Series. As shown, the permanent magnet in FIG. 2 is poled to have a north pole at one end and a south pole at the other end, although the polarity may be reversed if so desired. The permanent magnet 10 is in direct contact with the bottom of the cup-shaped member 12, and it is spaced and insulated from the inner surface of the side of the cup-shaped member by any appropriate means, such as insulating tape. The top end of the permanent magnet is displaced down from the rim of cup-shaped member 12.

The permanent magnet 10, as well as the cup-shaped member 12 are readily available on the market, and there is no need for any modification in the individual elements. The magnet 10 may be sealed in the cup-shaped member 12 by a layer 16, for example, of epoxy resin, or any other appropriate sealant, for protective purposes.

The first component of the unit of the invention, namely the cup-shaped member 12 and magnet 10 are embedded in the denture to be retained in the mouth of the patient. Grooves may be formed on the external surface of the cup to assist in retaining the cup embedded in the denture.

A second component of the unit, namely a low coercivity magnetic keeper 18 formed, for example, of ferromagnetic material, is mounted in a countersunk well in the upper surface of an exposed root in the mouth of the patient, which is intended to anchor the denture in place. The magnetic keeper 18 may be mounted on the root in any appropriate manner. For example, it may incorporate a stem 20 which extends passively down the canal of the root, and which has two or three threads at its upper end which permit the keeper to be threaded to the root. The keeper 18 and stem 20 may be cemented in place by an appropriate adhesive. Alternatively, the keeper 18 may be attached to a stem of appropriate semi-precious material which extends passively down into the root canal and which is cemented in place in the root. The keeper 18 may be formed of low coercivity magnetic material, such as ferromagnetic stainless steel of the 400 Series.

The diameter of the keeper 18 is such that is extends across the open end of cup-shaped member 12 to engage the side of the cup, and to enclose the open end. The keeper 18 is spaced from the permanent magnet 10, and this spacing may be increased or decreased by selecting the length of the permanent magnet, so as to achieve any desired magnetic strength for the retention unit.

When the denture is in place, the magnet 10 is completely enclosed in the cup-shaped member 12 by the keeper 18. The cup-shaped member and the keeper form a low reluctance magnetic path for the magnetic field of the permanent magnet, so that the field is substantially completely enclosed, and there is no external field to affect the hard and soft tissues in the mouth of the patient.

The invention provides, therefore, a simple magnetic retention unit for retaining dentures in the mouth of the patient, which can be assembled from readily available components, and which is simple to install in the denture and in the mouth of the patient.

It will be appreciated that while a particular embodiment of the invention has been shown and described, modifications may be made, and it is intended in the claims to cover all modifications which come within the true spirit and scope of the invention.

What is claimed is:

1. A denture magnetic retention unit comprising: a first component in the form of a cup-shaped member of low coercivity magnetic material having an open top, and a disc-shaped permanent magnet with magnetic poles on the opposite sides thereof retained within said cup-shaped member with one side of said disc-shaped permanent magnet contacting the bottom of the cup-shaped member; and a second component in the form of a keeper of low coercivity magnetic material positioned to extend across the open top of said cup-shaped member completely to enclose said permanent magnet within said cup-shaped member, said cup-shaped member and said keeper forming a low reluctance magnetic path for the magnetic field of the permanent magnet and serving to close the magnetic field of the permanent magnet when the denture is in place.

2. The denture magnetic retention unit defined in claim 1, in which said first component is adapted to be embedded in the denture, and said second component is adapted to be embedded in an exposed root of a tooth in the mouth of a patient.

3. The denture magnetic retention unit defined in claim 2, in which said cup-shaped member and said keeper are formed of a ferromagnetic stainless steel.

4. The denture magnetic retention unit defined in claim 1, in which the other side of the disc-shaped permanent magnet is displaced inwardly from the open top of said cup-shaped member.

5. The denture magnetic retention unit defined in claim 1, in which the permanent magnet is a cobalt/samarium alloy.

6. The denture magnetic retention unit defined in claim 1, in which the peripheral edge of said disc-shaped permanent magnet is spaced and insulated from the inner surface of the side of said cup-shaped member.

7. The denture magnetic retention unit defined in claim 4, in which the open top of the cup-shaped member is filled with a sealant of nonmagnetic material.

* * * * *